(12) United States Patent
Haake et al.

(10) Patent No.: US 8,858,923 B2
(45) Date of Patent: Oct. 14, 2014

(54) HAIR RELAXER

(75) Inventors: Hans-Martin Haake, Erkrath (DE); Ralf Bohlander, Erkrath (DE); Jessica Cecchini, Paris (FR); Mehmet Yücel Altunok, Düsseldorf (DE); Albrecht Weiss, Langenfeld (DE); Angela Brands, Meerbusch (DE)

(73) Assignee: Cognis IP Management GmbH, Duesseldorf (DE)

( * ) Notice: Subject to any disclaimer, the term of this patent is extended or adjusted under 35 U.S.C. 154(b) by 54 days.

(21) Appl. No.: 13/379,788

(22) PCT Filed: Jun. 17, 2010

(86) PCT No.: PCT/EP2010/003650
§ 371 (c)(1),
(2), (4) Date: Apr. 25, 2012

(87) PCT Pub. No.: WO2010/149311
PCT Pub. Date: Dec. 29, 2010

(65) Prior Publication Data
US 2012/0201776 A1    Aug. 9, 2012

(30) Foreign Application Priority Data

Jun. 26, 2009 (DE) .......................... 10 2009 030 859

(51) Int. Cl.
*A61K 8/30* (2006.01)
*A61K 8/00* (2006.01)
*A61K 8/19* (2006.01)
*A61K 8/25* (2006.01)
*A61Q 5/04* (2006.01)

(52) U.S. Cl.
CPC ... *A61K 8/25* (2013.01); *A61K 8/19* (2013.01); *A61Q 5/04* (2013.01)
USPC ...................................... 424/70.31; 424/70.1

(58) Field of Classification Search
CPC ......... A61K 8/062; A61K 8/042; A61K 8/33; A61Q 5/04; C08L 83/02
See application file for complete search history.

(56) References Cited

U.S. PATENT DOCUMENTS

| 3,973,574 | A  | * | 8/1976  | Minagawa et al. ........... 132/204 |
| 5,599,531 | A  |   | 2/1997  | Holcomb |
| 7,118,736 | B2 | * | 10/2006 | Cannell et al. ............. 424/70.51 |
| 2006/0228316 | A1 |   | 10/2006 | Cannell et al. |
| 2013/0037044 | A1 | * | 2/2013  | Plos et al. ...................... 132/204 |

FOREIGN PATENT DOCUMENTS

| EP | 1242039       | 9/2002 |
| FR | 1514179       | 1/1968 |
| WO | WO-95/03031   | 2/1995 |
| WO | WO-2009/040149 | 4/2009 |
| ZA | 7203489       | 6/1971 |

OTHER PUBLICATIONS

Sodium Metasilicate (http://en.wikipedia.org/wiki/Sodium_silicate (downloaded on Jul. 9, 2013)).*
Machine Translation of FR 1514179, 21 pgs., Feb. 28, 1968.
PCT International Search Report in PCT/EP2010/003650, dated May 2, 2011, 1 pg.
Ogawa, S. et al., "A curing method for permanent hair straightening using thioglycolic and dithiodiglycolic acids", *J. Cosmet. Sci.*, 51 Nov./Dec. 2000, 379-399.

* cited by examiner

*Primary Examiner* — Michael G Hartley
*Assistant Examiner* — Sun Y Kim
(74) *Attorney, Agent, or Firm* — Servilla Whitney LLC

(57) ABSTRACT

The invention relates to a hair smoothing agent characterized by a content of sodium silicate.

3 Claims, No Drawings

HAIR RELAXER

CROSS-REFERENCE TO RELATED APPLICATIONS

This application is the national stage entry of PCT/EP2010/003650, filed on Jun. 17, 2010, which claims priority to German Patent application number 102009030859.8, filed on Jun. 26, 2009, both of which are incorporated herein by reference in their entireties.

FIELD OF THE INVENTION

The invention is in the field of chemical hair smoothing agents and in particular in the field of hydroxide-based hair smoothing agents.

BACKGROUND

Hair smoothing is understood as meaning the straightening of wavy hair. For this, mechanical methods using heat in the form of e.g. smoothing irons in combination with haircare agents are understood just as much as chemical methods which penetrate into the structure of the hair. In the case of the chemical hair smoothing agents, also called hair relaxers, a distinction is made between agents based on thioglycolates, i.e. a reversed permanent wave, and the basic (lye-based) and the so-called non-basic (no-lye) relaxers. The latter use guanidinium hydroxide and are supposed to be less skin-irritating. They generally consist of two components, a cream base and a likewise basic activator, a concentrated solution of guanidinium carbonate in water.

The former are preparations based on sodium, potassium or lithium hydroxides. Depending on the hair structure, different amounts of hydroxide are incorporated into creams or gels in order to ensure simple handling coupled with adequate protection of the scalp at the same time.

However, it is common to all of these chemical hair smoothers of the prior art that they are firstly very aggressive towards the scalp and can lead to irritations, and secondly the application leads to significant damage of the hair. The hair becomes split and brittle to an extent which cannot be compensated for by subsequent treatment with conditioners.

The object of the present patent application was therefore to provide chemical hair smoothing agents which have less hair damage than the current market products. At the same time, these hair smoothing agents should have greater skin compatibility and thus be easier to use, including by the end customers.

SUMMARY

One aspect of the invention relates to a hair smoothing agent comprising waterglass in a cosmetically acceptable medium. Another aspect of the invention relates to a concentrate for the preparation of a hair smoothing agent, the concentrate comprising 1 to 65% by weight of waterglass, 0.5 to 80% by weight of alkyl polyglycosides, 0 to 50% by weight of glycerol, 0 to 5% by weight of a complexing agent and 0 to 10% by weight of sodium hydroxide. A third aspect of the invention accordingly relates to a process for the preparation of a hair smoothing agent, the process comprising stirring this concentrate into an end formulation. Yet another aspect of the invention relates to a process for the preparation of a hair smoothing agent, the process comprising stirring a solution of waterglass and optionally alkali metal or alkaline earth metal hydroxide into an O/W emulsion directly prior to use.

DETAILED DESCRIPTION

Surprisingly, it has now been found that hair smoothing agents characterized in that they comprise waterglass in a cosmetically acceptable medium do not have the aforementioned disadvantages. Coupled with smoothing effect that is just as good as that for hair smoothing agents merely rendered basic with alkali, the preparations according to the invention damage the hair structure to a considerably lesser extent than those of the prior art.

Waterglasses are glassy, water-soluble alkali metal silicates (i.e. salts of silicic acids) solidified from the molten mass, or viscous aqueous solutions thereof. In the case of standard commercial molten-glass-based waterglass, there are typically 1-4 mol of $SiO_2$ per 1 mol of alkali metal oxide ($M_2O$), for which reason waterglass solutions are usually also characterized by the weight ratio or molar ratio of $SiO_2$/alkali metal oxide and also the density of the aqueous solution. They comprise oligomeric silicate anions with alkali metal or quaternary nitrogen atoms as counterions (where e.g. M=K, Na, Li, Cs, $NR_4^+$). Particularly preferred waterglasses are sodium or potassium waterglasses. The soluble silicates are preferably used as aqueous solutions which comprise 15 to 60% by weight of solids.

The solutions can be modified very easily by the further additions of base. In this connection, for the use in cosmetic agents, preference is given to those waterglasses whose molar ratio of $SiO_2:M_2O$ (where M=alkali metal) is in the range from 0.03 to 2 and is preferably in the range from 0.1 to 1. Very particularly preferably, the range is from 0.3 to 0.8. The soluble silicates measured as $SiO_2$ are present in the aqueous phase of the hair smoothing agents according to the invention in amounts of from 0.01 to 8% by weight, preferably 0.05 to 5% by weight and particularly preferably from 0.1 to 2% by weight.

The solutions can be prepared for the aqueous phase by dissolving glass pieces from the smelting process or by hydrothermal preparation by dissolving diverse conceivable $SiO_2$ sources (sand, cristobalite, amorphous silicas, fly ashes, silica sols or silica gels) in hydroxide solutions. It is likewise possible to also dissolve hydrated alkali metal silicate powder in water directly prior to use by the user.

Reduced hair damage also arises when the hair smoothing agents according to the invention comprise, as well as the waterglass component, following separate addition, further alkali metal and/or alkaline earth metal hydroxide. Consequently, the present invention further provides hair smoothing agents which, as well as waterglass, also comprise alkali metal and/or alkaline earth metal hydroxides, preferably sodium hydroxide. In this connection, it has been found that a use of waterglass: alkali metal/alkaline earth metal hydroxide upon separate addition to the formulations in a quantitative ratio of 1:20 to 5:1 is particularly advantageous.

Often, the no-lye formulations already specified at the start are used; these comprise guanidine carbonates and have a lower irritation and/or skin damage potential than the compositions based only on alkali metal or alkaline earth metal hydroxides. The use of waterglass with or without the further addition of alkali metal or alkaline earth metal hydroxides surprisingly leads, even in the no-lye formulations, to considerably less damage of hair and scalp than in the formulations without waterglass. Consequently, the present invention further provides a hair smoothing agent comprising waterglass and optionally alkali metal and/or alkaline earth metal hydroxide and guanidine carbonate.

The hair smoothing agents according to the invention are further characterized in that they comprise an O/W emulsion as cosmetically acceptable medium. This emulsion must be stable particularly at alkaline pH values since the hair smoothing agents according to the invention have a pH of preferably greater than or equal to 12. Emulsifiers are therefore compounds of the hydroxypropylmethylcellulose, hydroxyethylcellulose, fatty alcohol sulfates type such as e.g. sodium cetearyl sulfate or sodium stearyl sulfate or further anionic emulsifiers of the acylamino acid type, particularly sodium stearoyl glutamates. Preference is given to an emulsion based on fatty alcohols and ethoxylated fatty alcohols in combination with further emulsifiers.

Emollients which can be used are, besides fatty alcohols, also Guerbet alcohols, such as e.g. octyldodecanol or dialkyl ethers such as e.g. dicaprylyl ether.

The present patent application furthermore provides a process for the preparation of a hair smoothing agent, characterized in that a solution of waterglass and optionally alkali metal and/or alkaline earth metal hydroxide is stirred into the cosmetically acceptable medium directly prior to using the hair smoothing agent. The cosmetically acceptable medium here can be present as O/W emulsion into which the aqueous solution of waterglass and optionally alkali metal and/or alkaline earth metal hydroxide is incorporated. However, the emulsion can also only be formed as a result of the incorporation of this aqueous solution.

Exceptional hair smoothing agents can be used particularly easily, thus both for the user and also in terms of process economics for manufacturers of hair smoothing agents, if the waterglass is used stabilized in a concentrate. This concentrate then only has to be added to the aqueous phase during the manufacture of the hair smoothing agent during the preparation of the emulsion. Consequently, this invention also relates to a concentrate for the preparation of a hair smoothing agent which comprises:

a) 1 to 65% by weight, preferably 15 to 50% by weight, of waterglass,
b) 0.5 to 80% by weight, preferably 5 to 25% by weight, of alkyl polyglycosides,
c) 0 to 50% by weight of glycerol,
d) 0 to 5% by weight, preferably 0.3 to 0.7% by weight, of a complexing agent and
e) 0 to 10% by weight of sodium hydroxide.

Alkyl polyglycosides are known nonionic surfactants which conform to the formula (I),

$$R^1O\text{—}[G]_p \qquad (I)$$

in which $R^1$ is an alkyl and/or alkenyl radical having 4 to 22 carbon atoms, G is a sugar radical having 5 or 6 carbon atoms and p is numbers from 1 to 10. The alkyl polyglycosides can be derived from aldoses or ketoses having 5 or 6 carbon atoms, preferably glucose. The preferred alkyl polyglycosides are thus alkyl and/or alkenyl oligoglucosides. The index number p in the general formula (I) indicates the degree of oligomerization (DP), i.e. the distribution of mono- and oligoglycosides and is a number between 1 and 10. Whereas p in a given compound must always be a whole number and here, in particular, can assume the values p=1 to 6, the value p for a specific alkyl polyglycoside is an analytically determined calculated parameter which in most cases is a fractional number. Preference is given to using alkyl polyglycosides with an average degree of oligomerization p of 1.1 to 3.0. The alkyl or alkenyl radical $R^1$ can be derived from primary alcohols having 4 to 11, preferably 8 to 10, carbon atoms. Typical examples are butanol, caproic alcohol, caprylic alcohol, capric alcohol and undecyl alcohol, and also technical-grade mixtures thereof, as are obtained, for example, during the hydrogenation of technical-grade fatty acid methyl esters or in the course of the hydrogenation of aldehydes from the Rolen oxo synthesis.

However, it is also possible to use other surfactants in the aforementioned concentrate instead of alkyl polyglycosides. Here, mention may be made in particular of the following with their INCI names and optionally trade names: Ethylhexyl Sulfate (Texapon® EHS) and/or Sodium Octyl Sulfate (Texapon® 842) and also fatty alcohol ethoxylates with alkyl chain lengths of 6 to 22 carbon atoms and from 1 to 150 ethoxy units.

Furthermore, it is possible to replace glycerol in the aforementioned concentrate by polyols. By way of example, mention may be made here of sugars such as glucose, sorbitol, but also natural products such as honey.

The complexing agents used in the aforementioned concentrate are preferably those which are stable at the high pH values of the preparations. By way of example, mention may be made of EDTA (ethylene-diaminetetraacetic acid), NTA (nitrilotriacetic acid) HEDP (1-hydroxyethane(1,1-diphosphonic acid)) and DTPA (diethylenetriaminepentaacetic acid).

EXAMPLES

Table 1 shows a standard hair smoothing agent of the prior art which only comprises sodium hydroxide, and a hair smoothing agent according to the invention comprising sodium hydroxide and waterglass. The cosmetically acceptable medium is identical for both preparations.

TABLE 1

Compositions of different hair smoothing agents

| Amounts in % by weight | INCI | Standard hair smoothing agent | Hair smoothing agent with waterglass |
|---|---|---|---|
| Phase A | | | |
| Emulgade 1000NI | Cetearyl Alcohol (and) Ceteareth-20 | 10 | 10 |
| Eumulgin SG | Sodium Stearoyl Glutamate | 0.2 | 0.2 |
| Lanette O | Cetearyl Alcohol | 4 | 4 |
| Paraffin | Paraffinum Liquidum | 10 | 10 |
| Vaseline | Petrolatum | 10 | 10 |
| Phase B | | | |
| Water | Aqua | ad 100 | ad 100 |
| Sodium hydroxide | Sodium Hydroxide (Pellets) | 2.2 | 1.5 |
| Waterglass potassium silicate | 13% $SiO_2$, 8% $K_2O$ | | 7.5 |
| pH 5% strength solution in water | | 12.4 | 12.3 |
| Achieved smoothing (=hair extension) in % | | 18.3 | 18.8 |
| Loss in the modulus of elasticity in % | | −57 | −28 |

These formulations were applied to tresses of curly Brazilian hair and left for 30 min. The smoothing agent was then rinsed out and the hair was shampooed. The hair was then dried. The achieved smoothing was determined by measuring the tress length before and after treatment. A triple determination was carried out. Here, it was found that the agent comprising waterglass achieved a slightly higher smoothing than the other agent.

Furthermore, the hair damage which occurred as a result of the smoothing treatment was quantified by means of stress/strain measurements. For this, a fully automated Dia-Stron MTT675 from Diastron, UK, was used. In order to prevent the measurement being influenced by atmospheric humidity, the tresses were covered with demineralized water for 60 min prior to the measurement and also remained in the water during the measurement. The hair strength was calculated from the ratio of the Young modulus before and after treatment (given in the table as loss of the modulus of elasticity in %). Since the measurements were carried out in the Hooke range, the same hair fibers could be measured before and after treatment.

These measurements revealed the superiority of the preparation according to the invention over that of the prior art. Significantly less damage to the hair occurred after treatment with waterglass.

TABLE 2

Hair smoothing agents prepared using a concentrate:

| Amounts in % by weight | INCI | Standard hair smoothing agent | Hair smoothing agent with concentrate |
|---|---|---|---|
| Phase A | | | |
| Paraffin | Paraffinum Liquidum | 15 | 15 |
| Lanette O | Cetearyl Alcohol | 6 | 6 |
| Eumulgin B 2 | Ceteareth-20 | 2 | 2 |
| Eumulgin B 3 | Ceteareth-30 | 2 | 2 |
| Phase B | | | |
| Water | Aqua | ad 100 | ad 100 |
| Sodium hydroxide | Sodium Hydroxide (Pellets) | 1.8 | 1.8 |
| Concentrate | see Table 3 | | 5.0 |
| pH 5% strength solution in water | | 12.2 | 12.1 |
| Achieved smoothing (=hair extension) in % | | 100% | 100% |
| Loss in the modulus of elasticity in % | | 75% | 53% |

The change in length was calculated by a different method to that in Table 1 since, in so doing, the original curliness of the tresses can be taken into consideration. Achieved smoothing=length of smoothed tress/maximum length of the tress. 100% thus means complete smoothing.

The concentrate used in Table 2 was prepared as follows:

TABLE 3

Concentrate composition

| Amounts in % by weight | INCI | Compound with waterglass |
|---|---|---|
| Plantacare 810 UP | Capryl Glucoside | 11.5 |
| Perpura 60 | 29% $SiO_2$, 30.3% $K_2O$ | 36.0 |
| Glycerol | Glycerin | 6.0 |
| Trilon BX | EDTA | 0.25 |
| Water | Aqua | ad 100 |
| pH 5% strength solution in water | | 12.35 |

Furthermore, a no-lye hair smoothing agent was also investigated.

TABLE 4

No-lye hair smoothing agent:

| Amounts in % by weight | Raw materials | INCI | Standard hair smoothing agent | Hair smoothing agent with waterglass | Hair smoothing agent with concentrate |
|---|---|---|---|---|---|
| | | Phase A | | | |
| 1. | Paraffin oil | Paraffinum Liquidum | 15.0 | 15.0 | 15.0 |
| | Lanette 14 | Mystristyl Alcohol | 10.0 | 10.0 | |
| | Lanette O | Cetearyl Alcohol | | | 6.0 |
| | Eumulgin B2 | Ceteareth-20 | 2.5 | 2.5 | 2.0 |
| | Eumulgin B3 | Ceteareth-30 | | | 2.0 |
| 2. | Water | Aqua | ad 100 | ad 100 | ad 100 |
| | PEG | Propylene glycol | 2.0 | 2.0 | 2.0 |
| | Lithium hydroxide | | 5.0 | 5.0 | 5.0 |
| | Waterglass | 13% $SiO_2$, 8% $K_2O$ | | 5.9 | |
| | Concentrate | see Table 3 | | | 5.0 |
| | | Phase B | | | |
| | Water | Aqua | ad 100 | ad 100 | ad 100 |
| | Dekafald | DMDM Hydantoin | 0.2 | 0.2 | 0.2 |
| | (Keltrol CG-SFT) | Xanthan Gum | 0.2 | 0.2 | 0.2 |
| | Guanidine carbonate | Guanidine Carbonate | 27.0 | 27.0 | 27.0 |
| pH 5% strength solution of the final mixture in water | | | 12.44 | 12.50 | 12.40 |
| Achieved smoothing (=hair extension) in % | | | 100% | 100% | 100% |
| Loss in the modulus of elasticity in % | | | 83% | 77% | 77% |

The compositions were prepared by, for phase A, melting the oil components and heating the water components and then mixing. 4 parts of phase A were mixed thoroughly directly prior to use with 1 part of phase B and applied to the hair. Loss in the modulus of elasticity was determined as described for Table 1, the achieved smoothing was determined as described for Table 2. In this connection, it is clearly evident that the preparations comprising waterglass have a significantly lower loss in the modulus of elasticity of the hair.

The invention claimed is:

1. A hair smoothing agent comprising soluble silicates in an amount in the range of 0.1 to 2 wt %, measured as $SiO_2$, in the aqueous phase of a cosmetically acceptable medium that is an O/W emulsion, which has a pH value of greater than or equal to 12, and an alkali metal hydroxide selected from sodium hydroxide, lithium hydroxide, or potassium hydroxide.

2. The hair smoothing agent of claim 1 further comprising guanidine carbonate.

3. A process for the preparation of a hair smoothing agent, the process comprising stirring a solution of soluble silicates and an alkali metal hydroxide selected from sodium hydroxide, lithium hydroxide, or potassium hydroxide into an O/W emulsion directly prior to use, wherein the soluble silicates are present in an amount in the range of 0.1 to 2 wt %, measured as $SiO_2$, in the aqueous phase of the O/W emulsion, which has a pH value of greater than or equal to 12.

* * * * *